United States Patent
Thakur et al.

(10) Patent No.: US 9,131,866 B2
(45) Date of Patent: Sep. 15, 2015

(54) AUGMENTED SIGNAL VECTOR ANALYSIS TO SUPPRESS GLOBAL ACTIVATION DURING ELECTROPHYSIOLOGY MAPPING

(71) Applicant: Boston Scientific Scimed, Inc., Maple Grove, MN (US)

(72) Inventors: Pramodsingh Hirasingh Thakur, Woodbury, MN (US); Barun Maskara, Blaine, MN (US); Allan C. Shuros, St. Paul, MN (US); Sunipa Saha, Shoreview, MN (US); Shibaji Shome, Arden Hills, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 13/923,012

(22) Filed: Jun. 20, 2013

(65) Prior Publication Data

US 2013/0345577 A1    Dec. 26, 2013

Related U.S. Application Data

(60) Provisional application No. 61/662,257, filed on Jun. 20, 2012.

(51) Int. Cl.
*A61B 5/0452* (2006.01)
*A61B 5/042* (2006.01)
*A61B 5/046* (2006.01)
(Continued)

(52) U.S. Cl.
CPC ............... *A61B 5/0422* (2013.01); *A61B 5/046* (2013.01); *A61B 5/6859* (2013.01); *A61B 18/1492* (2013.01)

(58) Field of Classification Search
CPC ...... A61B 5/024; A61B 5/0452; A61B 5/046; A61B 5/0422
USPC .......................................... 600/509, 512, 513
See application file for complete search history.

(56) References Cited

U.S. PATENT DOCUMENTS

| 4,407,296 A | 10/1983 | Anderson |
| 5,647,870 A | 7/1997 | Kordis et al. |

(Continued)

FOREIGN PATENT DOCUMENTS

| WO | WO0045700 A1 | 8/2000 |
| WO | WO0047278 A1 | 8/2000 |

(Continued)

OTHER PUBLICATIONS

International Search Report and Written Opinion issued in International Application No. PCT/US2013/046843, mailed Oct. 23, 2013, 12 pages.

(Continued)

*Primary Examiner* — Christopher D Koharski
*Assistant Examiner* — Michael Carey
(74) *Attorney, Agent, or Firm* — Faegre Baker Daniels LLP

(57) ABSTRACT

Electrical activity propagation along an electrode array within a cardiac chamber is reconstructed. Signals are sampled from the electrode array including signals from a channel of interest. An N-dimensional signal vector is then constructed using signals from N neighboring channels referenced to the channel of interest. A change in the N-dimensional signal vector over time is then determined and compared to a predetermined threshold to establish whether local activation has occurred on the channel of interest.

13 Claims, 3 Drawing Sheets

(51) Int. Cl.
*A61B 5/00* (2006.01)
*A61B 18/14* (2006.01)

(56) References Cited

U.S. PATENT DOCUMENTS

| | | | |
|---|---|---|---|
| 6,070,094 | A | 5/2000 | Swanson et al. |
| 6,214,025 | B1 | 4/2001 | Thistle et al. |
| 6,233,491 | B1 | 5/2001 | Kordis et al. |
| 6,660,021 | B1 | 12/2003 | Palmer et al. |
| 6,735,465 | B2 | 5/2004 | Panescu |
| 7,338,512 | B2 | 3/2008 | McGuckin, Jr. et al. |
| 7,780,694 | B2 | 8/2010 | Palmer et al. |
| 7,850,708 | B2 | 12/2010 | Pal |
| 8,165,666 | B1 | 4/2012 | Briggs et al. |
| 2005/0154321 | A1 | 7/2005 | Wolinsky et al. |
| 2005/0209678 | A1 | 9/2005 | Henkes et al. |
| 2006/0253044 | A1 | 11/2006 | Zhang et al. |
| 2008/0243214 | A1* | 10/2008 | Koblish ............ 607/115 |
| 2008/0281369 | A1 | 11/2008 | KenKnight et al. |
| 2009/0240157 | A1 | 9/2009 | Lian et al. |
| 2009/0254140 | A1 | 10/2009 | Rosenberg et al. |
| 2009/0306732 | A1 | 12/2009 | Rosenberg et al. |
| 2009/0318995 | A1 | 12/2009 | Keel et al. |
| 2010/0152801 | A1 | 6/2010 | Koh et al. |
| 2010/0268059 | A1 | 10/2010 | Ryu et al. |
| 2011/0054559 | A1 | 3/2011 | Rosenberg et al. |
| 2011/0054560 | A1 | 3/2011 | Rosenberg et al. |
| 2011/0066201 | A1 | 3/2011 | Rosenberg et al. |
| 2011/0066202 | A1 | 3/2011 | Rosenberg et al. |
| 2011/0066203 | A1 | 3/2011 | Rosenberg et al. |
| 2011/0092809 | A1 | 4/2011 | Nguyen et al. |
| 2011/0118803 | A1 | 5/2011 | Hou et al. |
| 2011/0144510 | A1 | 6/2011 | Ryu et al. |
| 2011/0184274 | A1 | 7/2011 | Rosenberg et al. |
| 2011/0213260 | A1 | 9/2011 | Keel et al. |
| 2011/0251505 | A1* | 10/2011 | Narayan et al. ............ 600/515 |
| 2011/0295137 | A1 | 12/2011 | Rosenberg et al. |
| 2011/0319954 | A1 | 12/2011 | Niazi et al. |
| 2013/0345537 | A1 | 12/2013 | Thakur et al. |
| 2013/0345583 | A1 | 12/2013 | Thakur et al. |

FOREIGN PATENT DOCUMENTS

| | | |
|---|---|---|
| WO | WO2006037172 A1 | 4/2006 |
| WO | WO2008118992 A1 | 10/2008 |

OTHER PUBLICATIONS

International Search Report and Written Opinion issued in PCT/US2013/046841, mailed Oct. 15, 2013, 12 pages.

Potter, M. et al., "Competing ICA Techniques in Biomedical Signal Analysis", Electrical and Computer Engineering, 2001, Canadian Conference on May 13-16, 2001, Piscataway, NJ, USA, IEEE, vol. 2, May 13, 2001, pp. 987-992.

Zhou, Yu et al., "A New United Analysis Method for Epicardial Mapping Signals", Bioinformatics and Biomedical Engineering, 2008, ICBBE 2008, the Second International Conference, IEEE, Piscataway, NJ, USA, May 16, 2008, pp. 636-639.

* cited by examiner

AUGMENTED SIGNAL VECTOR ANALYSIS TO SUPPRESS GLOBAL ACTIVATION DURING ELECTROPHYSIOLOGY MAPPING

CROSS-REFERENCE TO RELATED APPLICATION

This application claims priority to Provisional Application No. 61/662,257, filed Jun. 20, 2012, which is herein incorporated by reference in its entirety.

TECHNICAL FIELD

The present disclosure relates to cardiac mapping systems. More particularly, the present disclosure relates to a cardiac mapping system configured to reconstruct electrical activity propagation along an electrode array within a cardiac chamber of interest by preserving local activity and suppressing far-field activity.

BACKGROUND

Diagnosing and treating heart rhythm disorders often involves the introduction of a catheter having a plurality of sensors/probes into the heart through the blood vessels of a patient. The sensors detect electric activity of the heart at sensor locations in the heart. The electric activity is generally processed into electrogram signals that represent the activation of the heart at the sensor locations.

In a simple heart rhythm disorder, the signal at each sensor location is generally consistent from beat to beat in timing and often in shape and number of its deflections, enabling identification of activation onsets at each sensor location. However, in a complex rhythm disorder, the signal at each sensor location from beat to beat may transition between one, several, and multiple deflections of various shapes. For instance, when a signal for a sensor location in AF includes 5, 7, 11 or more deflections, it is difficult if not impossible to identify which deflections in the signal are at or near the sensor location in the heart (i.e., local activation) versus a further removed location still sensed by the sensor in the heart (i.e., far-field activation) or simply noise from another part of the patient's heart, other anatomic structures, movement or motion of the sensor relative to the heart or external electronic systems.

SUMMARY

Disclosed herein are various embodiments of a method for discriminating between local activation signals and far-field activity in a cardiac mapping system, as well as cardiac mapping systems employing such methods.

In Example 1, a method for reconstructing electrical activity propagation along an electrode array within a cardiac chamber includes sampling signals from the electrode array including signals from a channel of interest and constructing an N-dimensional signal vector using signals from N neighboring channels referenced to the channel of interest. The method further includes determining a change in the N-dimensional signal vector over time and comparing the change to a predetermined threshold to establish whether local activation has occurred on the channel of interest.

In Example 2, the method according to Example 1, wherein constructing the N-dimensional signal vector comprises finding a difference between a signal on the channel of interest at a sampling time and a signal on each of the other channels at the sampling time.

In Example 3, the method according to either Example 1 or Example 2, wherein the difference is adjusted based on latencies of sampled far-field signals.

In Example 4, the method according to any of Examples 1-3, wherein constructing the N-dimensional signal vector further comprises weighting the difference between the signal on the channel of interest the signal on each of the other channels at the sampling time to account for scaling differences.

In Example 5, the method according to any of Examples 1-4, wherein sampling the signals comprises including channels designed or biased toward picking up global activity in the multi-dimensional space to enhance discrimination on other channels.

In Example 6, the method according to any of Examples 1-5, wherein sampling the signals comprises employing an extended bipolar configuration with the electrode array.

In Example 7, the method according to any of Examples 1-6, wherein employing an extended bipolar configuration comprises sampling signals from most opposed electrodes located on the electrode array.

In Example 8, a mapping system includes an electrode array configured to reconstruct electrical activity propagation within a cardiac chamber according to the method of claims 1-7.

In Example 9, a mapping system for reconstructing electrical activity propagation within a cardiac chamber includes an array of mapping electrodes configured to sample signals from a channel of interest, and a processing device associated with the plurality of mapping electrodes, the processing device configured to record the sampled signals and associate one of the plurality of mapping electrodes with each recorded signal, the mapping processor further configured to construct an N-dimensional signal vector using signals from N neighboring channels referenced to the channel of interest, determine a change in the N-dimensional signal vector over time, and comparing the change to a predetermined threshold to establish whether local activation has occurred on the channel of interest.

In Example 10, the mapping system of Example 9, wherein to construct the N-dimensional signal vector, the processing device is further configured to find a difference between a signal on the channel of interest at a sampling time and a signal on each of the other channels at the sampling time.

In Example 11, the mapping system of either Examples 9 or 10, wherein the difference is adjusted based on latencies of sampled far-field signals.

In Example 12, the mapping system of any of Examples 9-11, wherein to construct the N-dimensional signal vector, the processing device is further configured to weight the difference between the signal on the channel of interest the signal on each of the other channels at the sampling time to account for scaling differences.

In Example 13, the mapping system of any one of Examples 9-12, wherein to sampling the signals, the processing device is further configured to bias a subset of channels towards picking up global activity in the multi-dimensional space to enhance discrimination on other channels.

In Example 14, the mapping system of any one of Examples 9-13, wherein to sample the signals, the processing device is further configured to employ an extended bipolar configuration on the array of mapping electrodes.

In Example 15, the mapping system of Example 14, wherein the processing system is further configured to employ the extended bipolar configuration at the most opposed electrodes located on the array of mapping electrodes.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
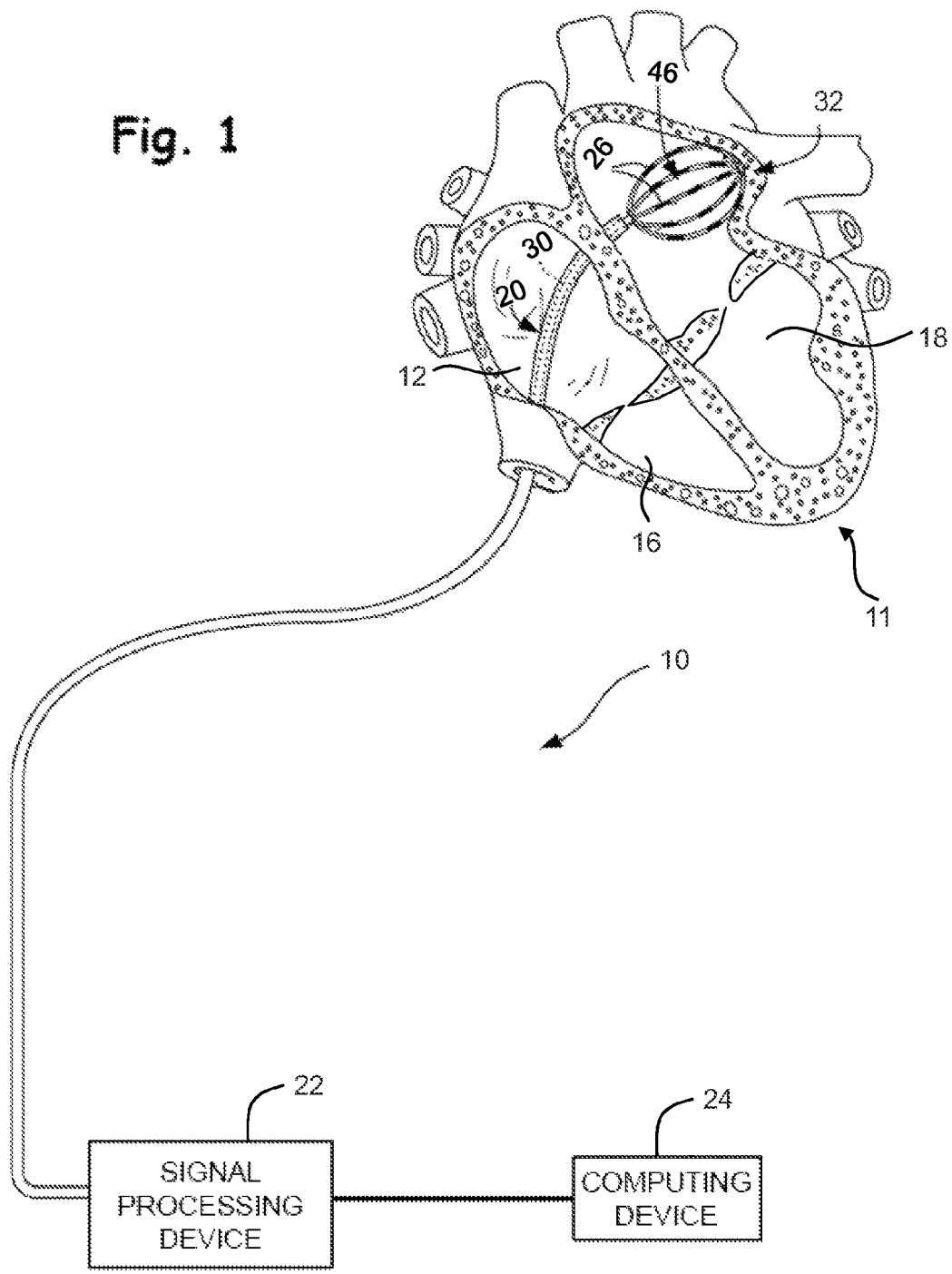
FIG. 1 illustrates an embodiment of a cardiac activation reconstruction system according to the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 illustrates an embodiment of a cardiac activation reconstruction system 10. The system 10 is configured to detect and reconstruct cardiac activation information collected/detected from a patient's heart 11 in connection with a heart rhythm disorder. The heart includes a right atrium 12, left atrium 14, right ventricle 16 and left ventricle 18.

The system 10 includes a catheter 20, a signal processing device 22, and a computing device 24. The catheter 20 is configured to detect cardiac activation information in the heart and to transmit the detected cardiac activation information to the signal processing device 22, either via a wireless or wired connection. The distal end of the catheter 20 includes a plurality of sensors 26, which can be inserted into the heart through the patient's blood vessels.

In some embodiments, one or more of sensors are not inserted into the patient's heart. For example, some sensors may detect cardiac activation via the patient's surface (e.g., electrocardiogram) or remotely without contact with the patient (e.g., magnetocardiogram). As another example, some sensors may also derive cardiac activation information from cardiac motion of a non-electrical sensing device (e.g., echocardiogram). In various embodiments or aspects, these sensors can be used separately or in different combinations, and further these separate or different combinations can also be used in combination with sensors inserted into the patient's heart.

The sensors 26, which are positioned at sensor locations in the heart under consideration (e.g., the left atrium in the illustrated embodiment), can detect cardiac activation information at the sensor locations. In some embodiments, an integral ablation electrode or a separate ablation catheter may be used to deliver energy to ablate the heart at or proximate the sensor locations.

The signal processing device 22 is configured to process (e.g., clarify and amplify) the cardiac activation information detected by the sensors 26 at the sensor locations into electrogram signals and to provide the processed cardiac signals to the computing device 24 for analysis or processing in accordance with various methods, such as those disclosed herein.

Figure 2:
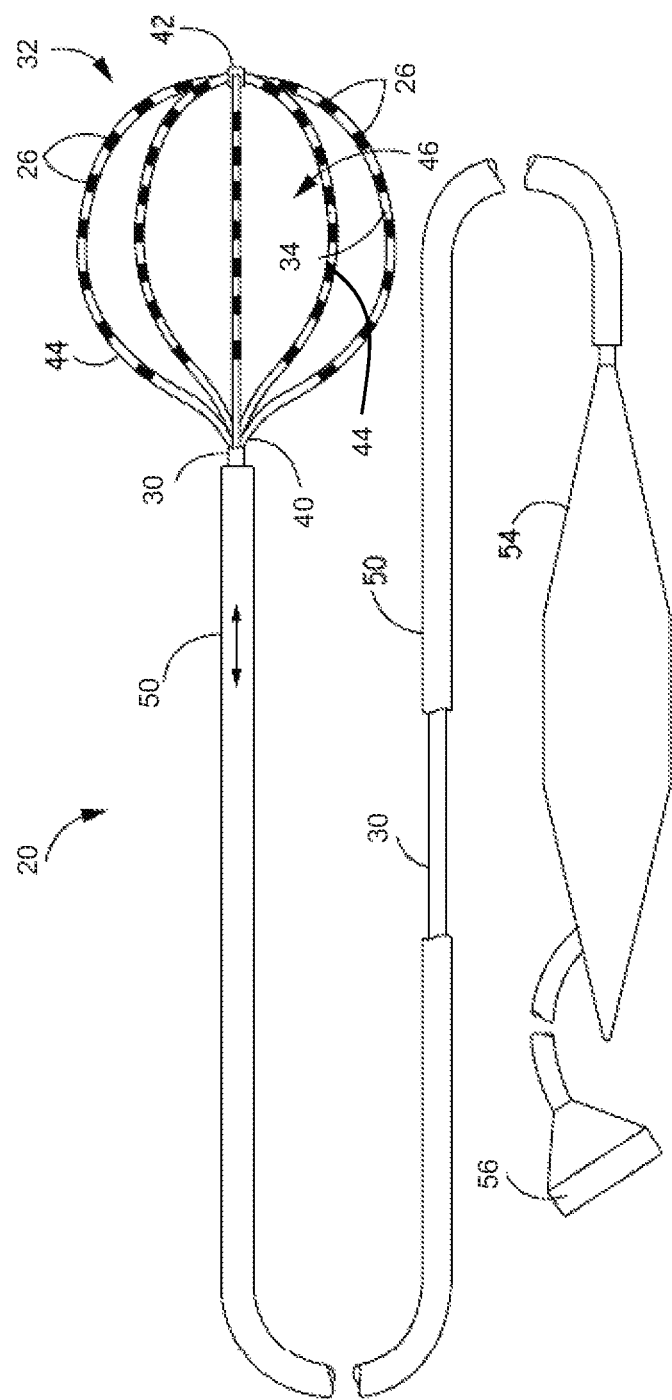
FIG. 2 illustrates an embodiment of a mapping catheter having a basket functional element carrying structure.

FIG. 2 illustrates an embodiment of a mapping catheter 20 including sensors at the distal end suitable for use in the system 10 shown in FIG. 1. The mapping catheter 20 that has a flexible catheter body 30, the distal end of which carries a three dimensional structure 32 configured to carry a plurality of mapping elements or sensors 26. In some embodiments, a proximity element 34 is preferably located adjacent each mapping element 26. Alternatively, the mapping elements 26 can be used as the proximity elements 34. As will be described in further detail below, the mapping elements 26 sense electrical activity in the heart tissue, which sensed activity is then processed by the signal processing device 22 and computing device 24 to assist the physician in identifying the site or sites having a heart rhythm disorder. This process is commonly referred to as mapping. This information can then be used to determine an appropriate location for applying appropriate therapy (e.g., ablation) to the identified sites.

The illustrated three dimensional structure 32 comprises a base member 40 and an end cap 42 between which flexible splines 44 generally extend in a circumferentially spaced relationship. As illustrated, the three dimensional structure 32 takes the form of a basket defining an open interior space 46. In some embodiments, the splines 44 are made of a resilient inert material, such as, e.g., Nitinol metal or silicone rubber, and are connected between the base member 40 and the end cap 42 in a resilient, pretensed condition, to bend and conform to the tissue surface they contact. In the illustrated embodiment, eight splines 44 form the three dimensional structure 32. Additional or fewer splines 44 could be used in other embodiments. As illustrated, each spline 44 carries eight mapping elements 26. Additional or fewer mapping elements 26 could be disposed on each spline 44 in other embodiments of the three dimensional structure 32. In the illustrated embodiment, the three dimensional structure 32 is relatively small (e.g., 40 mm or less in diameter). In alternative embodiments, the three dimensional structure 32 is larger (e.g., 40 mm in diameter or greater).

A slidable sheath 50 is movable along the major axis of the catheter body 30. Moving the sheath 50 forward (i.e., toward the distal end) causes the sheath 50 to move over the three dimensional structure 32, thereby collapsing the structure 32 into a compact, low profile condition suitable for introduction into an interior space, such as, for example, into the heart 12. In contrast, moving the sheath 19 rearward (i.e., toward the proximal end) frees the three dimensional structure 32, allowing the structure 32 to spring open and assume the pretensed position illustrated in FIG. 2. Further details of embodiments of the three dimensional structure 20 are disclosed in U.S. Pat. No. 5,647,870, entitled "Multiple Electrode Support Structures," the disclosure of which is expressly and fully incorporated by reference.

A signal wire (not shown) is electrically coupled to each mapping element 26. The wires extend through the body 30 of the mapping catheter 20 into a handle 54, in which they are coupled to an external connector 56, which may be a multiple pin connector. The connector 56 electrically couples the mapping elements 26 to the signal processing device 22 and computing device 24. Further details on mapping systems and methods for processing signal generated by the mapping catheter are discussed in U.S. Pat. No. 6,070,094, entitled "Systems and Methods for Guiding Movable Electrode Elements within Multiple-Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are expressly and fully incorporated herein by reference. In a similar manner, a signal wire electrically couples each proximity element 34 to the signal processing device 22 and computing device 24.

It is noted that other three dimensional structures could be deployed on the distal end. It is further noted that the multiple mapping elements 26 may be disposed on more than one structure rather than, for example, the single mapping catheter 20 illustrated in FIG. 2. For example, if mapping within the left atrium 14 with multiple mapping structures, an arrangement comprising a coronary sinus catheter carrying multiple mapping elements and a basket catheter carrying multiple mapping elements positioned in the left atrium 14 may be used. As another example, if mapping within the right atrium 12 with multiple mapping structures, an arrangement comprising a decapolar catheter carrying multiple mapping elements for positioning in the coronary sinus, and a loop catheter carrying multiple mapping elements for positioning around the tricuspid annulus may be used.

Additionally, although the mapping elements 26 have been described as being carried by mapping dedicated probes, such as mapping catheter 20, mapping elements can be carried on non-mapping dedicated probes. For example, an ablation catheter can be configured to include one or mapping elements disposed on the distal end of the catheter body and coupled to the signal processing device 22 and computing device 24. As another example, the ablation electrode at the distal end of the ablation catheter may be coupled to the signal processing device 22 and computing device 24 to also operate as a mapping electrode.

Figure 3A:
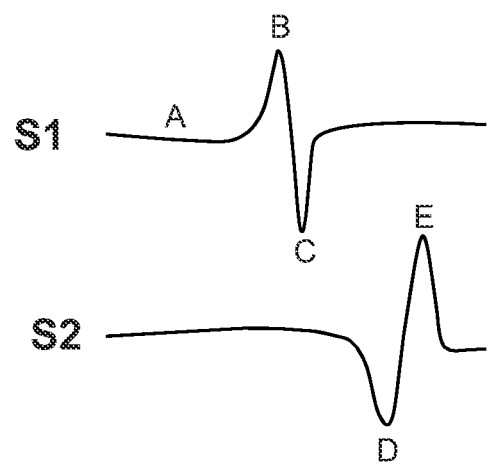
FIG. 3A illustrates an example of a plot of two channels from mapping elements of the basket functional element as a function of time.
Figure 3B:
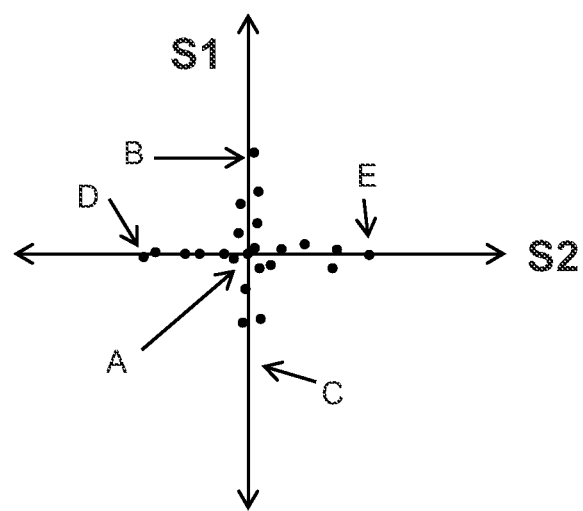
FIG. 3B illustrates an example of a plot using signals of two channels in the array of mapping elements in two-dimensional space.

In various embodiments, signals sensed by mapping elements 26 can be plotted to generate a multi-dimensional representation of signals from multiple elements or channels. FIGS. 3A illustrates an example of a plot of two channels (S1, S2) from the mapping elements 26 as a function of time. For example, in the embodiment illustrated in FIG. 2, channels S1 and S2 may be signals from a selected two of the sixty-four mapping elements 26. FIG. 3B illustrates an example of a plot using signals from two channels in the array of mapping elements 26 in two-dimensional space, with signal samples at various points in time for channel S1 plotted along the vertical axis and signal samples at various points in time for channel S2 plotted along the horizontal axis. The signals from channel S1 at points in time A, B, and C shown in FIG. 3A are shown plotted in FIG. 3B along the vertical axis, the signals from channel S2 at points in time D and E in FIG. 3A are shown plotted in FIG. 3B along the horizontal axis. While two channels are shown, any number of channels may be plotted to generate a multi-dimensional (or, N-dimensional) representation of signals from a corresponding number of channels.

According to the present disclosure, the N-dimensional representation of signals can be processed by the signal processing device 22 and/or computing device 24 to suppress signals due to global activation (i.e., far-field activity) to enhance signals associated with local activation. In some embodiments, signals are sampled across some or all of the channels (i.e., mapping electrodes 26) of the three-dimensional structure 32. Then, the signal processing device 22 and/or computing device 24 constructs an N-dimensional signal vector V(t) using signals from N neighboring channels referenced to a channel of interest. For example, in the case of unipolar EGMs, an array of bipolar is constructed using neighboring signals referenced to a central signal. If $S_0$ is the channel of interest, the N-dimensional signal vector V(t) can be expressed as:

$$V(t)=[S_1(t)-S_0(t), S_2(t)-S_0(t), \ldots, S_N(t)-S_0(t)]^T \quad \text{(Equation 1)}$$

where $S_0(t), \ldots, S_N(t)$ is the signal value at time t for each of channels $S_0$–$S_N$. Alternatively, the N-dimensional signal vector V(t) can be expressed as:

$$V(t)=[S_0(t)-S_1(t), S_0(t)-S_2(t), \ldots, S_0(t)-S_N(t)]^T \quad \text{(Equation 2)}$$

To determine whether local activation has occurred on the channel $S_0$, the change in V(t) over time (i.e., the time derivative of V(t)) is determined and compared to a threshold.

$$\left\| \frac{dV(t)}{dt} \right\| > TH$$

If the above inequality is true, then this is indicative that a local activation has occurred on channel $S_0$. In this approach, local activation is preserved, but global activation is decimated due to common mode with the neighboring N channels. The global activation is decimated by a factor of $\sqrt{N}$, so a greater number of neighboring channels results in a greater decimation of global activation signals. In some embodiments, the difference operations between signals to determine V(t) may be weighted to account for scaling differences between neighboring channels for a more extensive decimation of the global activation signals.

In some instances, the far-field signal may not appear instantaneously on all channels, but may exhibit a characteristic delay or a latency associated with volume propagation characteristic of the far-field component propagating through tissue. In scenarios where latencies are identified and/or expected, both Equation 1 and Equation 2 can be modified to account for the latencies associated with various electrodes. For example, if far-field signals emerge at latencies of $\omega_1, \omega_2, \ldots, \omega_N$ over the N neighboring electrodes with respect to a far-field reference signal such as a surface ECG, Equation 2 can be expressed as:

$$V(t)=[S_0(t)-S_1(t+\omega_1), S_0(t)-S_2(t+\omega_2), \ldots, S_0(t)-S_N(t+\omega_N)]^T \quad \text{(Equation 3)}$$

The latencies can be estimated by tracking the peaks or other characteristic features of the far-field signal on each channel with respect to the peaks or other characteristic feature of the corresponding R-wave sensed by the surface ECG. The estimated latencies can be averaged over multiple local heart beats.

In some embodiments, a subset of the channels (e.g., channels S1 and S2) sampled may be selected to bias toward picking up global activity in the N-dimensional space to enhance discrimination on other channels. For example, mapping elements 26 distal from the tissue may be referenced to other elements that generate far field interference to help with discriminating between far-field and local activations. In some embodiments, the selected channels may be the most opposed electrodes located on the three dimensional structure 32 to assess global atrial activity (i.e., extended bipolar configuration).

The method and system as described provides a flexible mathematical framework that can work with any number of channels on a mapping catheter (e.g., neighboring 8, neighboring 16, all at once, two groups of local and far-field). The ability to process information from any number of channels provides a more faithful reconstruction of electrical activity propagation in the chamber of interest compared to conventional paired channel comparisons for discriminating far-field activity from local activity.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for reconstructing electrical activity propagation along an electrode array within a cardiac chamber, the method comprising:
   sampling signals from the electrode array including signals from a channel of interest to generate a first plurality of signal samples and a second plurality of signal samples, the first plurality of signal samples corresponding to the channel of interest, and the second plurality of signal samples corresponding to N neighboring channels;
   constructing an N-dimensional signal vector, wherein each dimension of the N-dimensional signal vector is a difference between a signal on the channel of interest at a sampling time and a signal on a neighboring channel at the sampling time, wherein the N neighboring channels comprise at least one neighboring channel;
   determining a change in the N-dimensional signal vector over time; and
   comparing the change to a predetermined threshold to establish whether local activation has occurred on the channel of interest.

2. The method of claim 1, wherein the difference is adjusted based on latencies of sampled far-field signals.

3. The method of claim 1, wherein constructing the N-dimensional signal vector further comprises:
   weighting the difference between the signal on the channel of interest and the signal on each of the other channels at the sampling time to account for scaling differences.

4. The method of claim 1, wherein sampling the signals comprises including a subset of channels designed or biased toward picking up global activity in the multi-dimensional space to enhance discrimination on other channels.

5. The method of claim 1, wherein sampling the signals comprises employing an extended bipolar configuration with the electrode array.

6. The method of claim 5, wherein employing an extended bipolar configuration comprises sampling signals from most opposed electrodes located on the electrode array.

7. A mapping system comprising an array of mapping electrodes coupled to processing system configured to reconstruct electrical activity propagation within a cardiac chamber according to the method of claim 1.

8. A mapping system for reconstructing electrical activity propagation within a cardiac chamber, comprising:
   an array of mapping electrodes configured to sample signals from a channel of interest and sample signals from N neighboring channels; and
   a processing device associated with the plurality of mapping electrodes, the processing device configured to record the sampled signals and associate one of the plurality of mapping electrodes with each recorded signal, the processing device further configured to construct an N-dimensional signal vector, wherein each dimension of the N-dimensional signal vector is a difference between a signal on the channel of interest at a sampling time and a signal on a neighboring channel at the sampling time, determine a change in the N-dimensional signal vector over time, and compare the change to a predetermined threshold to establish whether local activation has occurred on the channel of interest, wherein the N neighboring channels comprise at least one neighboring channel.

9. The mapping system of claim 8, wherein the difference is adjusted based on latencies of sampled far-field signals.

10. The mapping system of claim 8, wherein to construct the N-dimensional signal vector, the processing device further configured to weight the difference between the signal on the channel of interest the signal on each of the other channels at the sampling time to account for scaling differences.

11. The mapping system of claim 8, wherein to sampling the signals, the processing device is further configured to bias a subset of channels towards picking up global activity in the multi-dimensional space to enhance discrimination on other channels.

12. The mapping system of claim 8, wherein to sample the signals, the processing device is further configured to employ an extended bipolar configuration on the array of mapping electrodes.

13. The mapping system of claim 12, wherein the processing device is further configured to employ the extended bipolar configuration at the most opposed electrodes located on the array of mapping electrodes.

* * * * *